(12) United States Patent
Zong et al.

(10) Patent No.: US 11,339,370 B2
(45) Date of Patent: May 24, 2022

(54) CELL LINE WITH METTL3 GENE KNOCKED OUT, ITS CONSTRUCTION METHOD AND INTERFERENCE VECTOR

(71) Applicant: ZHEJIANG UNIVERSITY, Zhejiang (CN)

(72) Inventors: Xin Zong, Zhejiang (CN); Yizhen Wang, Zhejiang (CN); Jing Zhao, Zhejiang (CN)

(73) Assignee: ZHEJIANG UNIVERSITY, Zhejiang (CN)

( * ) Notice: Subject to any disclaimer, the term of this patent is extended or adjusted under 35 U.S.C. 154(b) by 0 days.

(21) Appl. No.: 17/417,764

(22) PCT Filed: Jul. 21, 2018

(86) PCT No.: PCT/CN2018/096554
§ 371 (c)(1),
(2) Date: Jun. 24, 2021

(87) PCT Pub. No.: WO2020/006787
PCT Pub. Date: Jan. 9, 2020

(65) Prior Publication Data
US 2022/0010272 A1   Jan. 13, 2022

(30) Foreign Application Priority Data
Jul. 5, 2018   (CN) .......................... 201810733097.5

(51) Int. Cl.
*C12N 5/071* (2010.01)
*C12N 15/113* (2010.01)
*C12N 15/86* (2006.01)

(52) U.S. Cl.
CPC ........ *C12N 5/0625* (2013.01); *C12N 15/1137* (2013.01); *C12N 15/86* (2013.01); *C12N 2310/14* (2013.01); *C12N 2310/531* (2013.01); *C12N 2740/15043* (2013.01)

(58) Field of Classification Search
CPC ................ C12N 15/1137; C12N 15/86; C12N 2310/531; C12N 2740/15043; C12N 5/0625
USPC .... 435/6.1, 91.1, 91.31, 455, 458; 536/23.1, 536/24.5
See application file for complete search history.

(56) References Cited

FOREIGN PATENT DOCUMENTS

CN        107349217        11/2017

OTHER PUBLICATIONS

Ma, Ziyu et al., METTL3 Regulates Expression of Pluripotent Genes in Porcine Pluripotent sStem Cells, Chinese Journal of Biotechnology, vol. 34, No. 3, Mar. 25, 2018, ISSN: 1000-3061.
Yang, Fan et al. (Construction and Identification of Double Gene Knockout Cell Model for RNA Methyltransferase-like in Human Bladder Cancer Cells), China Occupational Medicine, vol. 44, No. 6, Dec. 31, 2017, ISSN: 2095-2619.
Isaia Barbieri, Promoter-bound METTL3 maintains myeloid leukaemia via m6A-dependent translation control, Nature. Dec. 7, 2017; 552(7683): 126-131.
Pedro J Batista et al., m6A RNA modification controls cell fate transitionin mammalian embryonic stem cells, Cell Stem Cell. Dec. 4, 2014; 15 (6):707-719.
Qi Cui et al. m6A RNA mETHYLATION regulates the self-renewal and tumorigenesis of glioblastoma stem cells, Cell Rep. Mar. 14, 2017; 18 (11): 2622-2634.
Zhihui Feng et al., METTL3 regulates alternative splicing of MyD88 upon the lipopolysaccharide-induced inflammatory response in human dental pulp cells, J. Cell. mol. Med. vol. 22, No. 5, 2018 pp. 2558-2568.
Yun Yang et al., Extensive translation of circular RNAs driven by N6-methyladenosine, Ceil research (2017) 27:626-641.

*Primary Examiner* — Jane J Zara

(57) ABSTRACT

A pig intestinal tract epithelium cell line with METTL3 gene knocked out and a construction method therefor. A gene interference vector for METTL3 form a pig is also provided.

3 Claims, 4 Drawing Sheets
Specification includes a Sequence Listing.

SEQUENCE LISTING

```
<160> NUMBER OF SEQ ID NOS: 5

<210> SEQ ID NO 1
<211> LENGTH: 2088
<212> TYPE: DNA
<213> ORGANISM: Sus scrofa
<220> FEATURE:
<223> OTHER INFORMATION: synthesized in laboratory

<400> SEQUENCE: 1
cactgaaaaa catatccgcc actccgctaa catttaaggt ggctcctcat ttcagttcca      60
aagcgagagc gaaacgggaa atgactttct atctggcgca tctctcagga cctccttccg     120
gttagccttg gggagtacgc gtgagagttg gaaatttcgt ggagccagtg ctgggaggtg     180
ctagtcggct accccttgtt cgagacgtgt cccggctgtg ggactaaaat gtcggacacg     240
tggagctcta tccaggccca caaaaagcag ctggactcgc tgagggaaag gctgcggcgg     300
aggcggaagc aggactcagg gcacttggat cttcggaatc cagaggcagc actgtctcca     360
accttccgta gtgacagccc agtgcctact gtacccactt ctggtggccc taagcccagc     420
acagcttcag cagttcctga gctagctaca gaccctgaat tagagaagaa gttgctacac     480
cacctttctg atctggcgct aacattgccc actgatgctg tctccatccg tcttgccatc     540
tccacgccag atgcccctgc cactcaggat ggagtggaaa gcctcttaca gaagtttgca     600
gctcaggagt tgattgaagt aaagcgaagt ctcctacaag atgatgcaca ccctactctt     660
gtgacctatg ctgatcattc caagctctct gccatgatgg gtgctgtggc agaaaagaag     720
ggccctgggg aggtagccgg gaccatcaca gggcagaaga ggcgtgcaga acaggactcg     780
accacagtag ctgcctttgc aagctctctg acctctggtc tggcctcttc agcatcagaa     840
gtagccaagg agccaaccaa gaaatcaagg aaacatgctg cctcagatgt tgacctggag     900
atagagagcc ttctgaacca acaatctact aaggaacaac agagcaagaa ggttagtcaa     960
```

-continued

```
gagatcctag aactattaaa tactacaaca gccaaggaac aatccattgt tgaaaagttt     1020
cgttcacgag gtcgggctca agtgcaagaa ttctgtgact atggaaccaa ggaggagtgc     1080
atgaaagcca gtgatgctga ccggccttgt cgcaagctgc acttcagacg gatcatcaat     1140
aaacacacgg atgagtcatt aggtgactgc tctttcctta acacatgttt ccacatggat     1200
acctgcaaat atgttcacta tgaaattgat gcttgcatgg attctgaggc tcctggaagc     1260
aaagaccata caccaagcca ggagcttgcc cttacacaga gcgttggagg ggactccaat     1320
gcagatcgac tcttcccacc tcagtggatc tgttgtgata ccgctacct ggacgtcagt      1380 atcttgggca gtttgcagt tgtgatggct gacccaccct gggatattca catggagctg      1440
ccctatggga ccctgacaga tgatgagatg cgcaggctca ataccagt actgcaggat       1500 gatggctttc tcttcctctg ggtcacaggc agggccatgg agttgggcag agaatgtctg     1560
aacctctggg gttacgaacg ggtagatgaa attatctggg tgaagacaaa tcaactgcag     1620
cgcatcattc ggacaggccg tacaggtcac tggttgaacc atgggaagga acactgcttg     1680
gttggtgtca aggaaatcc ccaaggattc aaccagggtc tggattgtga tgtgatcgta      1740
gccgaggttc gttccaccag tcataaacca gatgaaatct atggcatgat tgagagactg     1800 tccctggca ctcgaaagat tgaattgttt ggacgaccac acaatgtgca acctaattgg      1860
atcacccttg gaaatcaact ggatgggatc catctactag acccagatgt ggttgcccgg     1920
ttcaagcaaa ggtatccaga tggtatcatc tctaaaccta agaatttata gaagtacttt     1980
gaaacctaag catccatggc catggctctt caggctgtac ctgaagagta atatttgtac     2040
aatagctttt attccttatt taaataaaag tttgtattgt agttggga                  2088

<210> SEQ ID NO 2
<211> LENGTH: 60
<212> TYPE: DNA
<213> ORGANISM: Artificial Sequence
<220> FEATURE:
<223> OTHER INFORMATION: synthesized in laboratory

<400> SEQUENCE: 2
accgggagat cctagaacta ttaaatctcg agatttaata gttctaggat ctcttttttg     60

<210> SEQ ID NO 3
<211> LENGTH: 60
<212> TYPE: DNA
<213> ORGANISM: Artificial Sequence
<220> FEATURE:
<223> OTHER INFORMATION: synthesized in laboratory

<400> SEQUENCE: 3
cgaacaaaaa agagatccta gaactattaa atctcgagat ttaatagttc taggatctcc     60

<210> SEQ ID NO 4
<211> LENGTH: 23
<212> TYPE: DNA
<213> ORGANISM: Artificial Sequence
<220> FEATURE:
<223> OTHER INFORMATION: synthesized in laboratory

<400> SEQUENCE: 4
gagggcctat ttcccatgat tcc                                             23

<210> SEQ ID NO 5
<211> LENGTH: 26
<212> TYPE: DNA
```

```
<213> ORGANISM: Artificial Sequence
<220> FEATURE:
<223> OTHER INFORMATION: synthesized in laboratory

<400> SEQUENCE: 5
acagtccgaa accccaaacg cacgaa                                            26
```

CELL LINE WITH METTL3 GENE KNOCKED OUT, ITS CONSTRUCTION METHOD AND INTERFERENCE VECTOR

BACKGROUND OF THE PRESENT INVENTION

Field of Invention

The present invention belongs to the field of gene engineering, and more particularly to a cell line with METTL 3 gene knocked out, its construction method and interference vector.

Description of Related Arts

As the intensive mode is widely used in pig production in China, pigs will be infected by pathogenic microorganisms during every growth link, which is easy to cause intestinal (barrier) damage, resulting in nutrient digestion and absorption disorders accompanied by resistance decrease and serious diarrhea. Among the main nutrients, fatty acids, as the main energy source, have a greater impact on the absorption and utilization. In response to this phenomenon, the commonly used measures are disease resistant breeding and long-term high-dose drug addition. Due to the problems of long generation cycle and low popularity rate, disease resistance breeding is difficult to promote in a large scale. Therefore, the commonly used measures are long-term high-dose addition of feed antibiotics and zinc oxide at present. However, the existing problems are also obvious: it is very easy to cause bacterial resistance, meat product residues, disturbance of intestinal microflora balance and environmental pollution. Therefore, it is urgent to find a new way to solve this problem.

The methylation modification of m6A is mainly located on the sixth nitrogen atom of adenosine A of mRNA, which is a dynamic and reversible RNA modification. Mettl3, as the methyltransferase of the methylation modification of m6A, usually forms a complex with Mettl14 to perform the function of writing m6A. It has been reported that the changes of RNA methylation level regulated by Mettl3 are involved in the whole process from gene transcription to protein translation. For example, knock-out of Mettl3 significantly improved the proliferation and self-renewal of glioma stem cells or stem-like cells (Cui et al., 2017); Mettl3 mediated the translation of m6A-dependent cir-RNA (Yang et al., 2017); Mettl3 regulated gene transcription and played the role of gene transcription switch by combining with the DNA promoter region (Barbieri et al., 2017); knock-out of Mettl3 prevented the cutting of MyD88, a key factor of inflammation related pathway, to prevent the occurrence of inflammatory reaction (Feng et al., 2018; Yizhou Jiang et al., 2017); Mettl3 promoted cell cycle progression in the process of adipogenic differentiation to promote fat production (Batista et al., 2014). However, its role in the absorption and transport of fatty acids has not been reported.

SUMMARY OF THE PRESENT INVENTION

In order to overcome the shortcomings of the conventional art, the present invention provides an Mettl3 gene knock-out cell line, its construction method and an interference vector thereof.

A method for constructing METTL3 gene knockout cell line, comprising: processing gene knockout by an m6A methyltransferase gene Mettl3 to obtain a pig intestinal epithelial cell line which is capable of tolerating LPS (lipopolysaccharide) stimulation led fatty acid absorption disorder.

The constructing method, comprises steps of:
(1) designing shRNA according to the m6A methyltransferase gene mettl3,
wherein sequence of the mettl3 is shown in SEQ ID No.1, and sequence of the shRNA is shown in SEQ ID No.2 and SEQ ID No.3.
(2) phosphorylating m6A methyltransferase gene mettl3 shRNA;
(3) connecting the phosphorylated mettl3 shRNA to Lentivirus Expression Vector to obtain a mettl3 shRNA lentivirus expression vector.
(4) enveloping the mettl3 shRNA lentivirus expression vector obtained in step (3) with 293A cells.
(5) infecting the mettl3 shRNA lentivirus obtained in step (4) with intestinal epithelial cells, and then by puromycin, screening and obtaining the intestinal epithelial cells which are genetically modified to knock out the m6A methyltransferase gene mettl3.

Preferably, the construction method of the mettl3 shRNA lentivirus expression vector comprises steps of:
step (1) digesting the expression vector of shRNA lentivirus by bbsI, and obtaining the linear vector by gel recovery;
step (2) obtaining phosphorylated mettl3 shRNA, and connecting the expression vector of prsi9-u6 lentivirus by T4 ligase.

The present invention further provides a pig intestinal epithelial cell line obtained by the constructing method which is resistant to LPS stimulation leading to fatty acid absorption disorder.

The utility model relates to a gene interference vector for a swine m6A methyltransferase gene mettl3, wherein:
the interference vector is a shRNA designed for the m6A methyltransferase gene mettl3, which is inserted into the shRNA Lentivirus Expression Vector to knock out the expression of mettl3 in intestinal epithelial cells.

The beneficial effects of the invention are as follows:
The invention disclosed a new function of Mettl3 gene, which was involved in regulating fatty acid absorption and transportation of intestinal epithelial cells, and provided a method for improving fatty acid absorption disorders caused by LPS stimulation through gene editing. This is the first invention on Mettl3 regulated the fatty acid absorption of intestinal epithelial cells. The analysis of transcription level and protein level showed that Mettl3 expression in intestinal epithelial cells with gene editing was significantly reduced. The validation experiment of fatty acid absorption function showed that the intestinal epithelial cells with gene editing could tolerate the fatty acid absorption disorder caused by LPS stimulation. The invention not only laid a foundation for studying the role of Mettl3 in fatty acid absorption process, but also improved the fatty acid absorption disorders caused by LPS stimulation by gene editing method.

The mean value of data represents three biological repeats, and the error line represents standard error (SE). Significance analysis * means P<0.05, ** means P<0.01.

Figure 4:
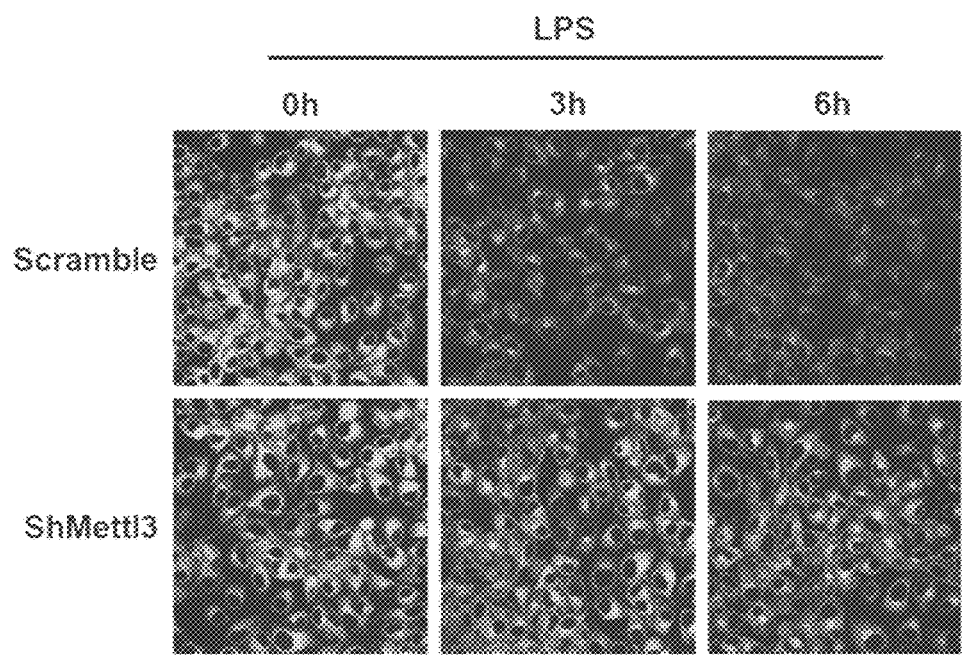
Figure 5:
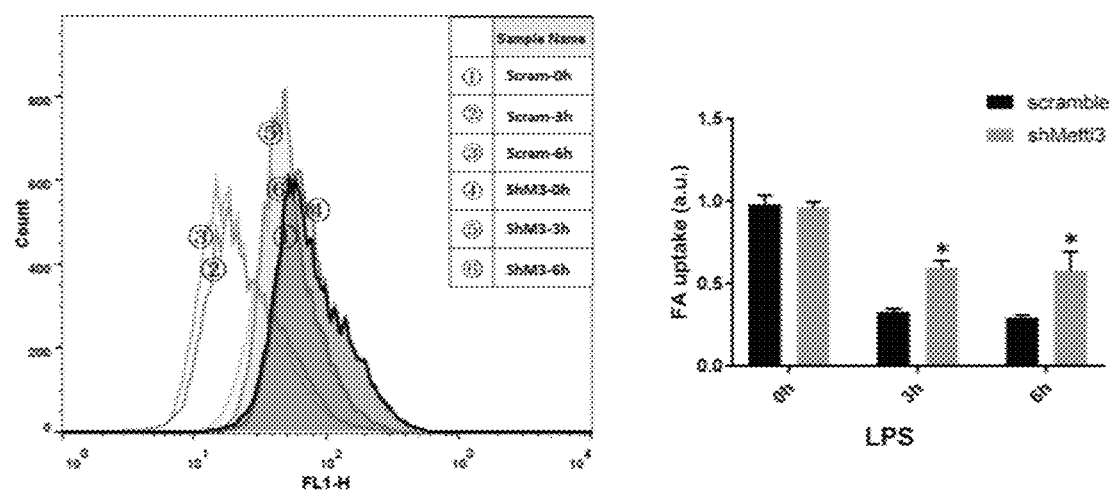

FIG. 4 is a diagram showing fatty acid absorption of gene editing intestinal epithelial cells edited by laser confocal scanning microscope;

FIG. 5 is a diagram showing fatty acid absorption of gene editing intestinal epithelial cells by flow cytometry. The left part is the fatty acid absorption of different treatment groups, and the right part is the quantitative statistics of the left figure. The average value of data represents three biological repeats. The error line represents the standard error (SE). Significance analysis * means P<0.05, ** means P<0.01.

Figure 6:
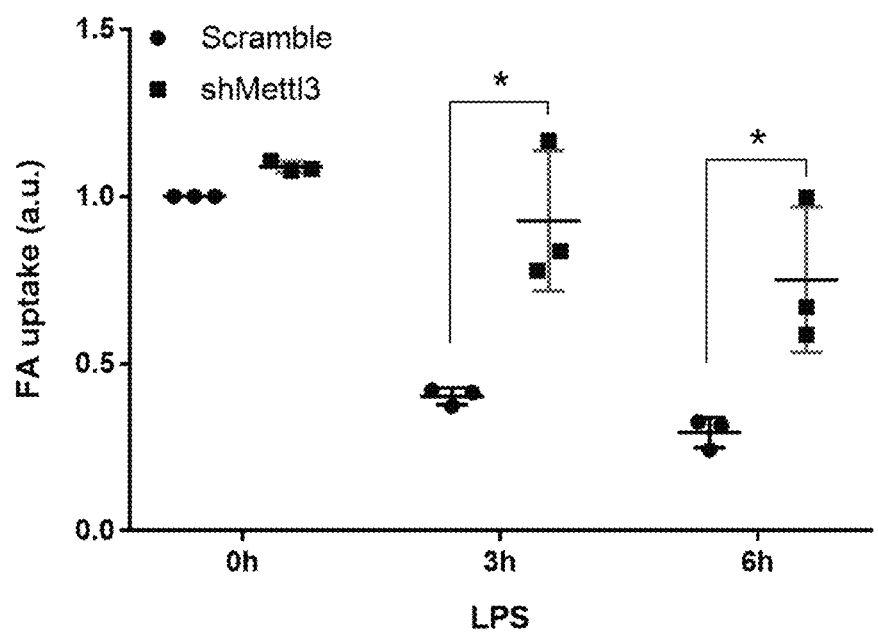

FIG. 6 is a diagram showing absorption of fatty acids in gene edited intestinal epithelial cells by ultraviolet spectrophotometry; the average value of data represents three biological repeats. The error line represents the standard error (SE). Significance analysis * means P<0.05, ** means P<0.01.

Figure 7:
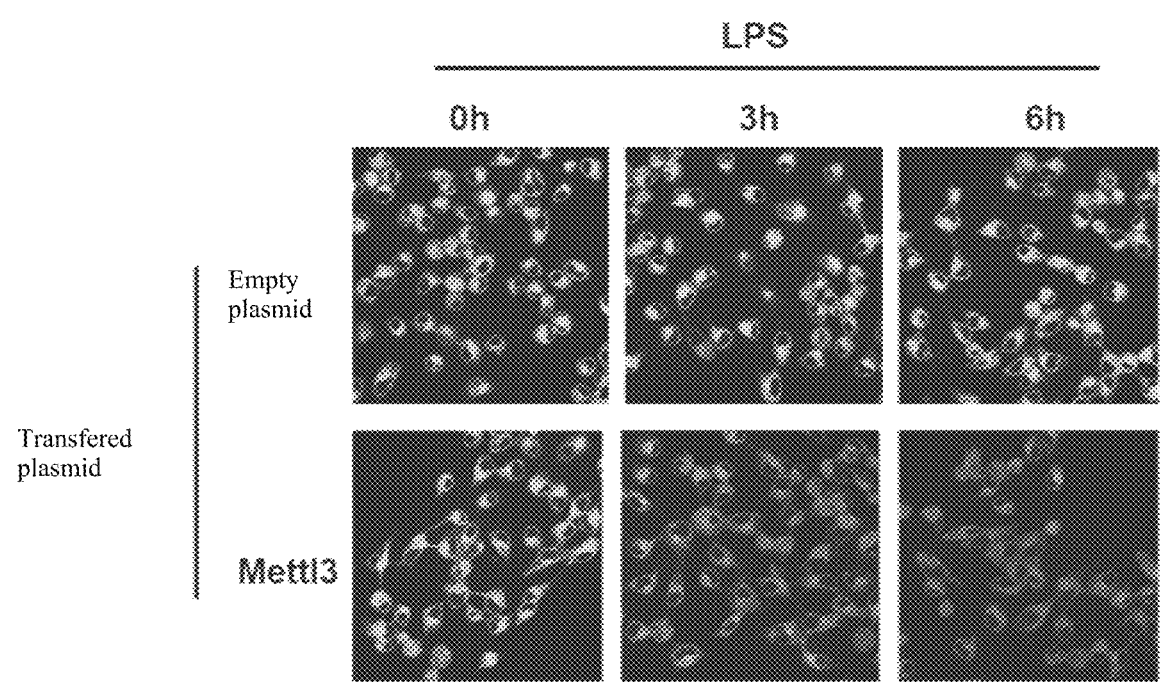

FIG. 7 is a diagram showing effect of Mettl3 plasmid infection on fatty acid absorption in Mettl3 knock-out intestinal epithelial cells.

DETAILED DESCRIPTION OF THE PREFERRED EMBODIMENT

The invention will be further described in combination with the attached drawings and embodiments.

Example 1. Acquisition of Mettl3 shRNA Lentivirus Expression Vector

Mettl3 shRNA in the invention was designed with online shRNA design tool: http://www.broadinstitute.org/rnai/public/seq/search; Mettl3 gene sequence is shown in SEQ ID No.1, shRNA sequence includes upstream sequence P1 and downstream sequence P2, as follows:

```
P1 (upstream sequence):
                                         (SEQ ID No. 2)
ACCGG GAGATCCTAGAACTATTAAAT CTCGAG ATTTAATAGTTCTAG

GATCTC TTTTTTG;

P2 (downstream sequence):
                                         (SEQ ID No. 3)
CGAACAAAAAA GAGATCCTAGAACTATTAAAT CTCGAG

ATTTAATAGTTCTAG GATCTC C.
```

Mettl3 shRNA was phosphorylated by T4 Polynucleotide Kinase at 37° C. for 30 minutes, then at 95° C. for 2 minutes and natural cooling to room temperature.

The expression vector of shRNA lentivirus was digested by BbsI and recovered by gel to obtain linear vector; the phosphorylated Mettl3 shRNA was incubated with T4 ligase at room temperature for 2 hours and then connected to the expression vector of pRSI9-U6 lentivirus. The strain DH5 α was transformed by heat-shock method and the plasmid was extracted for PCR identification. The primer sequence is as follows.

```
                                         (SEQ ID NO. 4)
Forward:    5'-GAGGGCCTATTTCCCATGATTCC-3', (SEQ ID NO. 5)
Reverse:    5'-ACAGTCCGAAACCCCAAACGCACGAA-3'.
```

Figure 1:
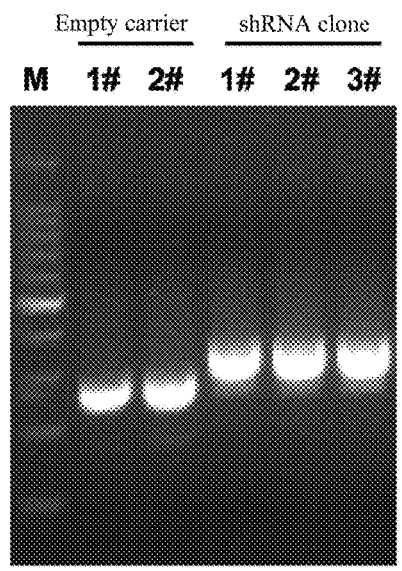
FIG. 1 is a Agarose gel electrophoresis to identify the Mettl3 shRNA lentivirus expression vector by PCR.
Figure 2:
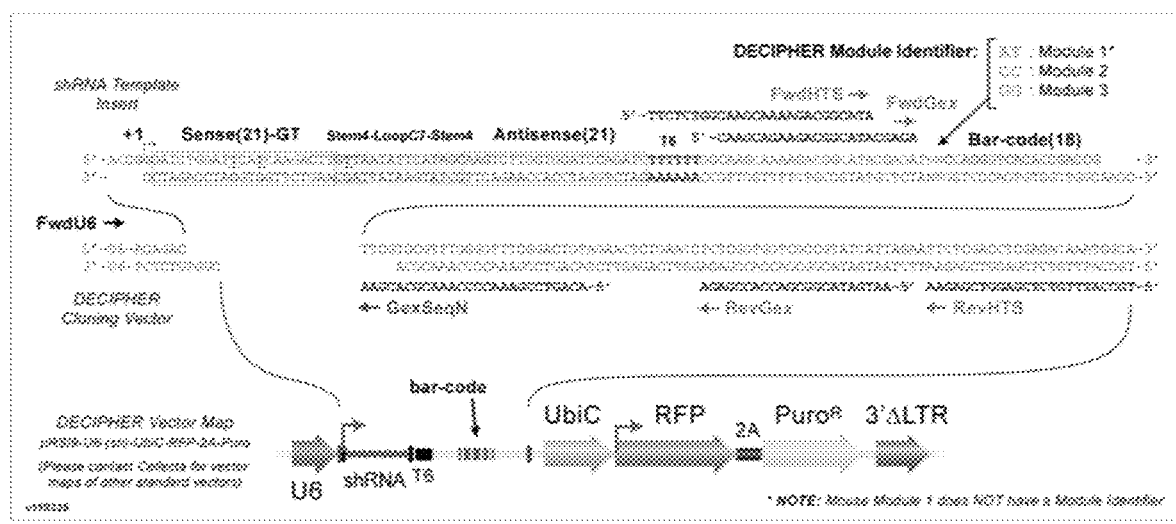
FIG. 2 is a schematic diagram of pRSI9-U6 lentivirus vector.

The reaction conditions were 94° C. pre-denaturation for 3 min, 94° C. denaturation for 15 s, 56° C. annealing for 30 s, 72° C. extension for 2 min, 25 reaction cycles to obtain the positive clones. As shown in FIG. 1, the PCR products of the selected clones were larger than those of the negative control group, indicating that the shRNA of Mettl3 was indeed inserted into the expression vector of pRSI9-U6 lentivirus as shown in FIG. 2.

Example 2. The Envelope of Mettl3 shRNA Lentivirus

2 μg of the Mettl3 shRNA lentivirus expression plasmid obtained by the method in Example 1 was transferred into lentivirus element 0.25 μg VSVG and 1 μg PsPax by lipofect Libo2000; after 24 hours, it was replaced with 1.5ml complete culture medium; after 48 hours, the virus was collected to obtain Mettl3 shRNA lentivirus.

Example 3. Gene Editing of Intestinal Epithelial Cell Line

Figure 3A:
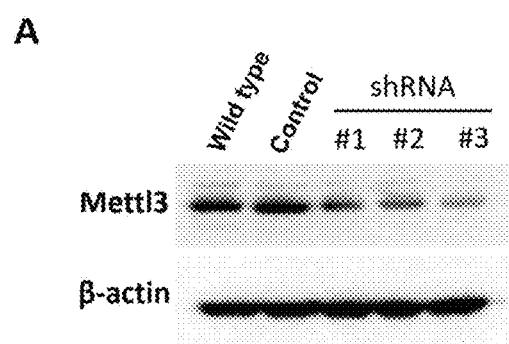
FIG. 3A is a diagram showing Western blot results of Mettl3 protein expression level after Mettl3 shRNA lentivirus infecting epithelial cells.
Figure 3B:
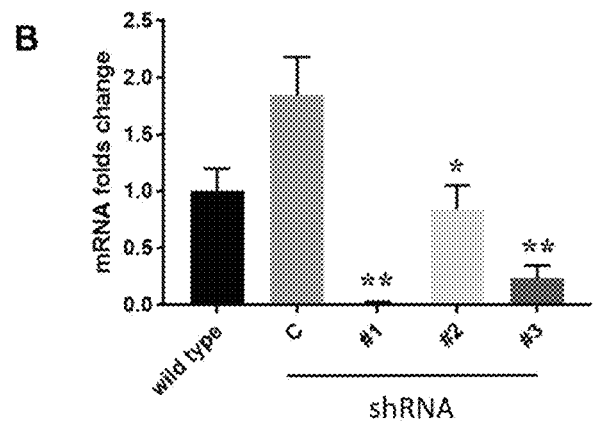
FIG. 3B is a diagram showing a transcription level of Mettl3 in intestinal epithelial cells after gene editing.

500 μL of the Mettl3 shRNA lentivirus obtained by the method in Example 2 was added to the intestinal epithelial cell IPEC-J2, which was transformed into a complete medium 24 hours later, and 4 μg/mL purinomycin was added 48 hours later for screening. Finally, the intestinal epithelial cell with Mettl3 gene edited was verified by fluorescent quantitative PCR and Western blot. As shown in FIG. 3A-3B, the expression level of Mettl3 in intestinal epithelial cells of the Mettl3 shRNA lentivirus infected group was significantly lower than that of the empty vector group.

Example 4. Analysis of Fatty Acid Absorption of Gene Edited Intestinal Epithelial Cells by Laser Confocal Method The Mettl3 knock-out intestinal epithelial cells obtained by the method in Example 3 were stimulated with 100 μg/mL lipopolysaccharide (LPS) for 0 hour, 3 hours or 6 hours respectively with normal cells (Scramble) as control; the fatty acids labeled with BODIPY were added and incubated at 37° C. for 5 minutes, and the absorption of fatty acids was detected by laser confocal. The results showed that the tolerance of Mettl3 knock-out intestinal epithelial cells to LPS stimulation induced fatty acid absorption disorder was significantly higher than that of normal cells. As shown in FIG. 4, LPS stimulation was carried out for the control group and Mettl3 knock-out intestinal epithelial cells respectively. The results showed that the absorption of fatty acids in the control group was significantly blocked under LPS stimulation, but Mettl3 knock-out intestinal epithelial cells showed obvious tolerance.

Example 5. Gene Editing of Fatty Acid Absorption in Intestinal Epithelial Cells by Flow Cytometry The Mettl3 knock-out intestinal epithelial cells obtained by the method in Example 3 were stimulated with 100 μg/mL lipopolysaccharide (LPS) for 0 hour, 3 hours or 6 hours respectively with normal cells (Scramble) as control;

the fatty acids labeled with BODIPY were added and incubated at 37° C. for 5 minutes, and the absorption of fatty acids was detected by 488 nm wavelength flow cytometry. The results showed that the tolerance of Mettl3 knock-out intestinal epithelial cells to LPS induced fatty acid absorption disorder was significantly higher than that of normal cells. As shown in FIG. 5, the control group (Scramble) and the Mettl3 knock-out intestinal epithelial cells (shMettl3) were stimulated with LPS for 0, 3 or 6 hours respectively.

Example 6. Detection of Fatty Acid Absorption in Gene Edited Intestinal Epithelial Cells by UV Spectrophotometry The normal and gene edited IPEC-J2 cells were seeded with gelatin coated, 96 well, black or transparent plates respectively. After overnight culture, the serum was starved for at least 8 hours with FBS free medium, treated with 1 mg/mL LPS for 0, 3, 6 hours, and then washed briefly with phosphate buffered saline (PBS). At the same time, add BODIPY FA (molecular probe γ-D3823) and fatty acid free bovine serum albumin (BSA) (2:1 molar ratio) into PBS and pre-incubate in 37° C. water bath for 10 minutes; after adding cells, incubate at 37° C. for 5 minutes, wash twice with PBS added with 0.5% BSA, each time for 2 min, in order to inhibit the extracellular fluorescence, add 0.4% trypan blue (50 µL per pore), and measure immediately with ultraviolet spectrophotometer. Intracellular fluorescence was measured (488 nm for excitation, 515 nm for emission, 495 nm for cut off). As shown in FIG. 6, the control group (Scramble) and the Mettl3 gene edited intestinal epithelial cells (shMettl3) were stimulated with LPS for 0, 3 and 6 hours respectively. The absorption of fluorescent labeled fatty acids was detected by UV spectrophotometry.

Example 7. Effect of Mettl3 Plasmid Infection on Fatty Acid Absorption of Intestinal Epithelial Cells The Mettl3 knock-out intestinal epithelial cells obtained by the method in Example 3 were transferred with pcDNA3.1empty plasmid and Mettl3 plasmid by Lipo2000. 24 hours later, 100 µg/mL LPS was used to stimulate for 0 hour, 3 hours, 6 hours respectively. The fatty acid labeled with BODIPY was added and incubated at 37° C. for 5 minutes. The absorption of fatty acid was detected by flow cytometry (wavelength 488 nm). The results showed that compared with the empty body group, the fatty acid absorption level of Mettl3 plasmid group decreased significantly under LPS stimulation, which indicated that Mettl3 played an important role in the tolerance of fatty acid absorption disorder. As shown in FIG. 7, the intestinal epithelial cells with Mettl3 gene knocked out by gene editing were transferred into pcDNA3.1 empty plasmid and Mettl3 plasmid, and then LPS stimulation treatment was carried out for 0 hour, 3 hours and 6 hours. The absorption of fluorescent labeled fatty acids was detected by confocal laser.

What is claimed is:

1. A method for constructing METTL3 gene knockout cell line, comprising: processing gene knockout by an m6A methyltransferase gene Mettl3 to obtain a pig intestinal epithelial cell line which is capable of tolerating LPS (lipopolysaccharide) stimulation led fatty acid absorption disorder;

comprising steps of:
(1) designing shRNA according to the m6A methyltransferase gene mettl3,
wherein sequence of the mettl3 is shown in SEQ ID No.1, and sequence of the shRNA is shown in SEQ ID No.2 and SEQ ID No.3;
(2) phosphorylating m6A methyltransferase gene mettl3 shRNA;
(3) connecting the phosphorylated mettl3 shRNA to Lentivirus Expression Vector to obtain a mettl3 shRNA lentivirus expression vector;
(4) enveloping the mettl3 shRNA lentivirus expression vector obtained in step (3) with 293A cells;
(5) infecting the mettl3 shRNA lentivirus obtained in step (4) with intestinal epithelial cells, and then by puromycin, screening and obtaining the intestinal epithelial cells which are genetically modified to knock out the m6A methyltransferase gene mettl3.

2. The method according to claim 1, wherein the construction method of the mettl3 shRNA lentivirus expression vector comprises steps of:
step (1) digesting the expression vector of shRNA lentivirus by bbsI, and obtaining the linear vector by gel recovery;
step (2) obraining phosphorylated mettl3 shRNA, and connecting the expression vector of prsi9-u6 lentivirus by T4 ligase.

3. A pig intestinal epithelial cell line obtained by the establishment method according to claim 1, which is resistant to LPS stimulation leading to fatty acid absorption disorder.

* * * * *